United States Patent [19]

Buckler et al.

[11] 4,226,992
[45] Oct. 7, 1980

[54] AMINO-FUNCTIONALIZED NAPHTHALENE-1,2-DICARBOXYLIC ACID HYDROZIDES

[75] Inventors: Robert T. Buckler, Edwardsburg, Mich.; Hartmut R. Schroeder, Elkhart, Ind.

[73] Assignee: Miles Laboratories, Inc., Elkhart, Ind.

[21] Appl. No.: 82,110

[22] Filed: Oct. 5, 1979

Related U.S. Application Data

[62] Division of Ser. No. 927,286, Jul. 24, 1978.

[51] Int. Cl.³ .................................. C07D 237/32
[52] U.S. Cl. .................................. 544/234
[58] Field of Search .................................. 544/234

[56] References Cited

U.S. PATENT DOCUMENTS 3,366,572  1/1968  Scott .................................. 252/188.3

OTHER PUBLICATIONS

Gundermann et al., Chem. Abs., 81, 90717p, (1974).
Schroeder et al., Chem. Abs., 89, 38942j, (1978).

*Primary Examiner*—Mark L. Berch
*Attorney, Agent, or Firm*—Andrew L. Klawitter

[57] ABSTRACT

Amino-functionalized naphthalene-1,2-dicarboxylic acid hydrazides of the formula:

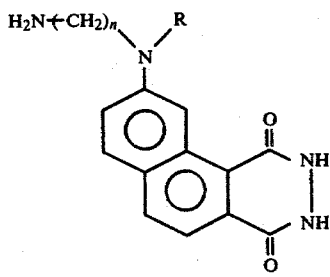

wherein R is hydrogen or straight chain alkyl containing 1-4 carbon atoms and n=2-6. The compounds are intermediates in the synthesis of chemiluminescent naphthalene-1,2-dicarboxylic acid hydrazide-labeled conjugates which are useful as reagents in specific binding assays for determining ligands or their specific binding partners in liquid media.

3 Claims, No Drawings

AMINO-FUNCTIONALIZED NAPHTHALENE-1,2-DICARBOXYLIC ACID HYDROZIDES

This is a division of application Ser. No. 927,286, filed July 24, 1978.

BACKGROUND OF THE INVENTION

1. FIELD OF THE INVENTION

This invention relates to novel chemiluminescent-labeled conjugates for use in specific binding assays for a ligand, such as an antigen, hapten or antibody, in a liquid medium such as a body fluid. The invention further relates to intermediate compounds produced in the synthesis of the novel labeled conjugates.

2. BRIEF DESCRIPTION OF THE PRIOR ART

Specific binding assay methods have undergone a technological evolution from the original competitive binding radioimmunoassay (RIA) in which a radioisotope-labeled antigen is made to compete with antigen from a test sample for binding to specific antibody. In the RIA technique, sample antigen is quantitated by measuring the proportion of radioactivity which becomes associated with the antibody by binding of the radio-labeled antigen (the bound-species of the labeled antigen) to the radioactivity that remains unassociated from antibody (the free-species) and then comparing that proportion to a standard curve. A comprehensive review of the RIA technique is provided by Skelly et al., Clin. Chem. 19:146(1973). While by definition RIA is based on the binding of specific antibody with an antigen or hapten, radiolabeled binding assays have been developed based on other specific binding interactions, such as between hormones and their binding proteins.

From the radiolabeled binding assays have evolved nonradioisotopic binding assays employing labeling substances such as enzymes as described in U.S. Pat. Nos. 3,654,090 and 3,817,837. Recently further improved nonradioisotopic binding assays have been developed as described in German Offenlegungschriften Nos. 2,618,419 and 2,618,511 based on U.S. Ser. Nos. 667,982 and 667,996, filed on Mar. 18, 1976 and assigned to the present assignee, employing particularly unique labeling substances, including coenzymes, cyclic reactants, cleavable fluorescent enzyme substrates, and chemiluminescent molecules. The chemiluminescent labels consist of an organic molecule which undergoes a change in chemical structure with the production of light.

Specific examples of substances useful as chemiluminescent labels mentioned in German OLS No. 2,618,511 are luminol, isoluminol, pyrogallol and luciferin. In particular, an example is provided in the OLS [and in Anal. Chem. 48:1933(1976) based on the same work] of an isoluminol-labeled conjugate wherein isoluminol is coupled through its amino function by a 2-hydroxypropylene bridge to the ligand biotin. The isoluminol-labeled conjugate is monitored in the binding assay by measuring the production of light in the presence of either hydrogen peroxide and peroxidase or potassium superoxide. The chemiluminescent phthalhydrazide-labeled conjugates wherein an amino-phthalhydrazide is coupled through its amino function by a 2-hydroxyalkylene bridge to a ligand are described in the U.S. patent application filed on even date herewith entitled "Chemiluminescent-Labeled Conjugates for Use in Specific Binding Assays" (Ser. No. 927,622) and assigned to the present assignee.

The efficiency of the amino-phthalhydrazides as chemiluminescent labels has been improved by coupling through the amino function with a straight chain lower alkylene bridge as described in the U.S. patent application filed on even date herewith entitled "Chemiluminescent Phthalhydrazide-Labeled Conjugates" (Ser. No. 927,621) and assigned to the present assignee. The use of more efficient labels enables more sensitive detection of ligands.

SUMMARY OF THE INVENTION

Labeled conjugates comprising even more efficient chemiluminescent labels have now been devised having the formula:

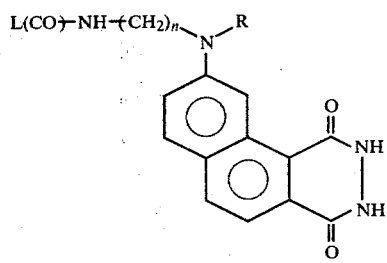

wherein R is hydrogen or straight chain alkyl containing 1-4 carbon atoms, preferably ethyl, n=2-6, preferably 4, and L(CO)— is a specifically bindable ligand, or a binding analog thereof, bound through an amide bond.

The subject chemiluminescent naphthalene-1,2-dicarboxylic acid hydrazide-labeled conjugates are used in specific binding assays for detecting the ligand or a binding partner thereof. The labeled conjugates are monitored in the performance of a binding assay by oxidizing the labeled conjugates and measuring the light produced either as total light produced or peak light intensity. For instance, a specific binding assay for determining a hapten in a liquid medium might be carried out by incubating a sample of the liquid medium with an antibody for such hapten and with a labeled conjugate of the present invention wherein such hapten or a binding analog is labeled with the subject chemiluminescent moiety. During the incubation, any hapten present in the liquid medium competes with the labeled conjugate for binding with the antibody. Thereafter, the amount of labeled conjugate resulting in the bound-species compared to the free-species (which amount is an inverse function of the amount of hapten in the liquid medium assayed) is determined (i.e., monitored) either in a homogeneous fashion, if the chemiluminescent character of the labeled conjugate is different when in the bound-species than when in the free-species, or in a heterogeneous fashion, if such character is essentially the same in both species. In the homogeneous assay, the unseparated reaction mixture containing both species of the labeled conjugate is combined with an appropriate oxidation system for the chemiluminescent label and the light produced is measured. In the heterogeneous assay, the bound- and free-species are separated by any conventional technique, the oxidation system combined with one thereof, and the light produced is measured.

The monitorable chemiluminescent reaction may be illustrated as follows:

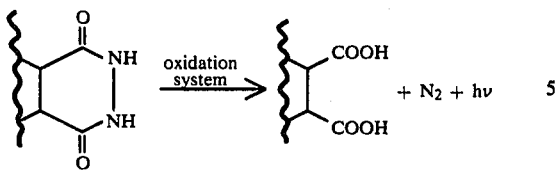

wherein hν represents electromagnetic radiation emitted. Useful oxidation systems include hydrogen peroxide combined with any of the following catalysts, peroxidase (particularly microperoxidase), catalase, deuterohemin, hematin or ferricyanide ions; hypochlorite ions combined with cobalt ions; persulfate ions; potassium superoxide; periodate ions; hypoxanthine combined with xanthine oxidase; or potassium t-butoxide.

The chemiluminescent-labeled conjugates may be employed in any conventional homogeneous or heterogeneous binding assay method, including competitive binding methods, sequential saturation methods, direct binding methods, and "sandwich" binding methods. Further details concerning the state of the art for binding assay techniques may be found in the aforementioned German OLS Nos. 2,618,419 and 2,618,511.

In the context of this disclosure, the following terms shall be defined as follows unless otherwise indicated: "specifically bindable ligand" is an organic substance of analytical interest for which there is a specific binding partner; "specific binding partner of the ligand" is the substance which has a noncovalent binding affinity for the ligand to the exclusion of other substances; and "binding analog of the ligand" is an organic substance which is different in chemical structure from the ligand but which behaves essentially the same as the ligand with respect to the binding affinity of the specific binding partner of the ligand.

The specifically bindable ligand or analog thereof in the present labeled conjugates, in terms of its chemical nature, usually is a protein, polypeptide, peptide, carbohydrate, glycoprotein, steroid, or other organic molecule for which a specific binding partner is obtainable. In functional terms, the ligand will usually be an antigen or an antibody thereto; a hapten or an antibody thereto; or a hormone, vitamin, or drug, or a receptor or binding substance therefor. Most commonly, the ligand is an immunologically-active polypeptide or protein of molecular weight between 1,000 and 4,000,000 such as an antigenic polypeptide or protein or an antibody; or is a hapten of molecular weight between 100 and 1,500.

The present labeled conjugates are prepared usually by forming a peptide or amide couple between (1) an amino derivative of a chemiluminescent naphthalene-1,2-dicarboxylic acid hydrazide and (2) either the ligand, where such contains a carboxylic acid function, or a binding analog of the ligand (e.g., a derivative of the ligand) which analog contains the desired carboxylic acid function. Such condensation reactions can be accomplished by reacting the amino derivative of the label directly with the carboxylic acid-containing ligand or ligand analog using conventional peptide condensation reactions such as the carbodiimide reaction [Science 144:1344 (1964)], the mixed anhydride reaction [Erlanger et al., Methods in Immunology and Immunochemistry, ed. Williams and Chase, Academic Press (New York 1967) p. 149], and the acid azide and active ester reactions [Kopple, Peptides and Amino Acids, W. A. Benjamin, Inc. (New York 1966)]. See also for a general review Clin. Chem. 22:726(1976).

It will be recognized, of course, that other well known methods are available for coupling the ligand or a derivative thereof to the amino-derivative of the label. In particular, conventional bifunctional coupling agents may be employed for coupling a ligand, or its derivative, containing a carboxylic acid or amino group to the amino-derivative of the label. For example, amine-amine coupling agents such as bis-isocyanates, bis-imidoesters and glutaraldehyde [Immunochem. 6:53(1969)] may be used to couple a ligand or derivative containing an amino group to the amino-derivative of the label. Also, appropriate coupling reactions are well known for inserting a bridge group in coupling an amine (e.g., the amino-derivative of the label) to a carboxylic acid (e.g., the ligand or a derivative thereof). Coupling reactions of this type are thoroughly discussed in the literature, for instance in the above-mentioned Kopple monograph and in Lowe & Dean, Affinity Chromatography, John Wiley & Sons (New York 1974).

Such coupling techniques will be considered equivalents to the previously discussed peptide condensation reactions in preparing useful labeled conjugates. The choice of coupling technique will depend on the functionalities available in the ligand or analog thereof for coupling to the label derivative and on the length of bridging group desired. In all cases, for purposes of this disclosure, the resulting labeled conjugate will comprise the label derivative bound to the remaining portion of the conjugate through an amide bond. Such remaining portion of the conjugate will be considered as a residue of a binding analog of the ligand, unless the ligand itself is directly coupled to the label derivative. Thus, in this description and in the claims to follow, the abbreviation L (CO+ represents the ligand or a binding analog thereof coupled through an amide bond, wherein such analog may be a derivative of the ligand coupled by peptide condensation to the label derivative or may be the ligand or derivative thereof coupled through a bridging group inserted by coupling of the ligand or derivative to the label derivative with a bifunctional coupling agent.

Preparation of the present chemiluminescent-labeled conjugates proceeds according to the following general synthetic sequence:

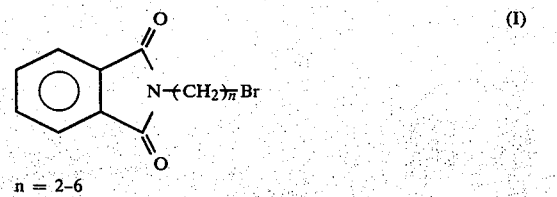

n = 2-6

Reaction of an N-(ω-bromoalkyl)phthalimide (I) [available from Aldrich Chemical Co., Milwaukee, Wisconsin USA, or see Derscherl and Weingarten, Justus Liebig's Annalen der Chemie 574:131(1951)] with dimethyl 7-aminonaphthalene-1,2-dicarboxylate [Gundermann et al, Justus Liebig's Annalen der Chemie 684:127(1965)] produces the intermediate dimethyl 7-[ω-N-(phthalimido)alkyl]aminonaphthalene-1,2-dicarboxylate (II).

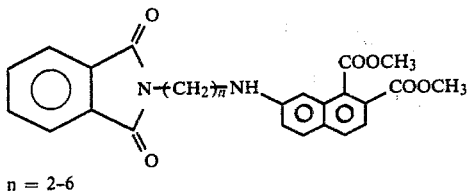

n = 2-6

Alkylation of the amine group in the intermediate dicarboxylate (II) is obtained by reaction with a dialkyl sulfate (III) [Rodd, *Chemistry of Carbon Compounds*, vol. 1, Elsevier Publ. Co. (New York 1951) p. 337]

m = 0-3 to yield the alkylated derivative (IV)

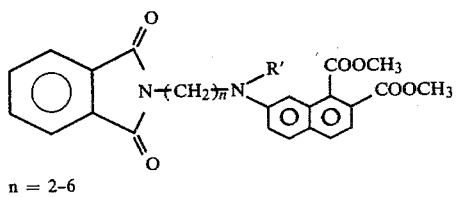

n = 2-6 wherein R' is straight chain alkyl containing 1–4 carbon atoms.

Treatment of the intermediate dicarboxylate (II) or the alkylated derivative (IV) with hydrazine produces the amino-hydrazide (V)

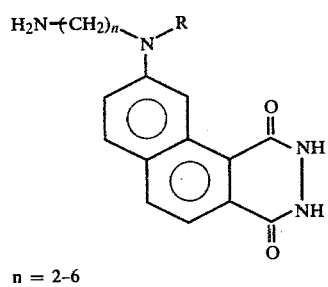

n = 2-6 wherein R is hydrogen or straight chain alkyl containing 1–4 carbon atoms.

Condensation of the amino-hydrazide (V) with (a) the ligand to be labeled, where such contains a carboxylic acid function, (b) a binding analog of the ligand, such analog being a carboxylic acid derivative of the ligand, or (c) the ligand or an appropriate derivative of the ligand in the presence of a bifunctional coupling agent, produces the chemiluminescent-labeled conjugate (VI)

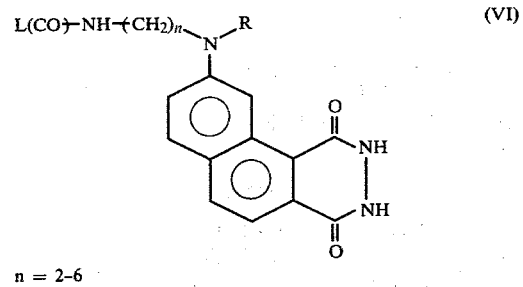

n = 2-6 wherein R is the same as defined above and L(CO)— represents the specifically bindable ligand, or a binding analog thereof (formed by derivation of the ligand and/or insertion of a bridge by a bifunctional coupling agent), bound through an amide bond.

Other variations of labeled conjugates based on the above-described synthetic scheme are clearly evident. In particular, various ring-substituted dimethyl 7-aminonaphthalene-1,2-dicarboxylates may be used as starting material to produce ring-substituted labeled conjugates possessing substantially the same qualitative properties as the conjugates prepared according to the above-described scheme. Such conjugates will be recognized as equivalents and are exemplified by the addition of one, two or more simple substituents to an available aromatic ring site, such substituents including without limitation, alkyl, e.g., methyl, ethyl and butyl; halo, e.g., chloro and bromo; nitro; hydroxyl; alkoxy, e.g., methoxy and ethoxy, and so forth.

As stated hereinabove, the ligand which is comprised in the labeled conjugage or whose binding analog is comprised in the labeled conjugate is in most circumstances an immunologically-active polypeptide or protein of molecular weight between 1,000 and 4,000,000 such as an antigenic polypeptide or protein or an antibody; or is a hapten of molecular weight between 100 and 1,500. Following will now be presented various methods for coupling such ligands or analogs thereof to the amino-derivative (V) of the label through an amide bond.

Polypeptides and Proteins

Representative of specifically bindable protein ligands are antibodies in general, particularly those of the IgG, IgE, IgM and IgA classes, for example hepatitis B antibodies; and antigenic proteins such as insulin, chorionic gonadotropin (e.g., HCG), carcinoembryonic antigen (CEA), myoglobin, hemoglobin, follicle stimulating hormone, human growth hromone, thyroid stimulating hormone (TSH), human placental lactogen, thyroxine binding globulin (TBG), instrinsic factor, transcobalamin, enzymes such as alkaline phosphatase and lactic dehydrogenase, and hepatitis-associated antigens such as hepatitis B surface antigen ($HB_sAg$), hepatitis e antigen ($HB_eAg$) and hepatitis core antigen ($HB_cAg$). Representative of polypeptide ligands are angiotensin I and II, C-peptide, oxytocin, vasopressin, neurophysin, gastrin, secretin, and glucagon.

Since, as peptides, ligands of this general category comprise numerous available carboxylic acid and amino groups, coupling to the amino-derivative of the chemiluminescent label can proceed according to conventional peptide condensation reactions such the carbodiimide reaction, the mixed anhydride reaction, and so forth as described hereinabove, or by the use of convention bifunctional reagents capable of coupling carboxylic acid or amino functions to the amino group in the label derivative as likewise described above. General references concerning the coupling of proteins to primary amines or carboxylic acids are mentioned in detail above.

Haptens

Haptens, as a class, offer a wide variety of organic substances which evoke an immunochemical response in a host animal only when injected in the form of an immunogen conjugate comprising the hapten coupled to a carrier molecule, almost always a protein such as albumin. The coupling reactions for forming the immunogen conjugates are well developed in the art and in general comprise the coupling of a carboxylic acid ligand or a carboxylic acid derivative of the ligand to available amino groups on the protein carrier by formation of an amide bond. Such well known coupling reactions are directly analogous to the present formation of labeled conjugates by coupling carboxylic acid ligands or binding analogs to the amino-derivative of the chemiluminescent label.

Hapten ligands which themselves contain carboxylic acid functions, and which thereby can be coupled directly to the amino-derivative of the label, include the iodothyronine hormones such as thyroxine and liothyronine, as well as other materials such as biotin, valproic acid, folic acid and certain prostaglandins. Following are representative synthetic routes for preparing carboxylic acid binding analogs of hapten ligands which themselves do not contain an available carboxylic acid function whereby such analogs can be coupled to the amino-derivative of the label by the aforementioned peptide condensation reactions or bifunctional coupling agent reactions (in the structural formulae below, n represents an integer, usually from 1 through 6).

Carbamazepine

Dibenz[b,f]azepine is treated sequentially with phosgene, an ω-aminoalkanol, and Jones reagent (chromium trioxide in sulfuric acid) according to the method of Singh, U.S. Pat. No. 4,048,511 to yield the following series of carboxylic acids:

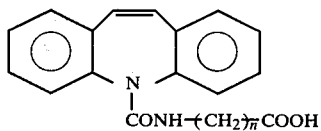

Quinidine

Following the method of Cook et al., *Pharmacologist* 17: 219(1975), quinidine is demethylated and treated with 5-bromovalerate followed by acid hydrolysis to yield a suitable carboxylic acid derivative.

Digoxin and Digitoxin

The aglycone of the cardiac glycoside is treated with succinic anhydride and pyridine according to the method of Oliver et al., *J. Clin. Invest.* 47:1035(1968) to yield the following:

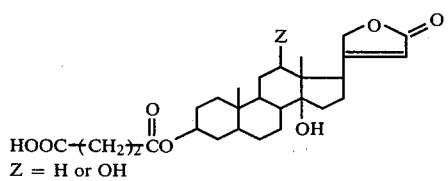

Z = H or OH

Theophylline

Following the method of Cook et al., *Res. Comm. Chem. Path. Pharm.* 13:497(1976), 4,5-diamino-1,3-dimethylpyrimidine-2,6-dione is heated with glutaric anhydride to yield the following:

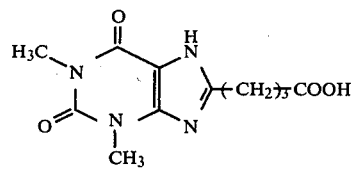

Phenobarbital and Primidone

Sodium phenobarbital is heated with methyl 5-bromovalerate and the product hydrolyzed to the corresponding acid derivative of phenobarbital [Cook et al., *Quantitative Analytic Studies in Epilepsy*, ed. Kelleway and Peterson, Raven Press (New York 1976) pp. 39-58]:

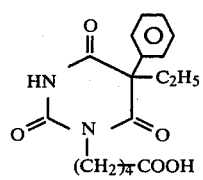

To obtain the acid derivative of primidone following the same Cook et al reference method, 2-thiophenobarbital is alkylated, hydrolyzed, and the product treated with Raney nickle to yield:

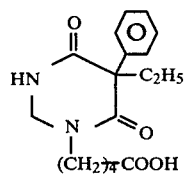

Diphenylhydantoin

Following the method of cook et al, *Res. Comm. Chem. Path. Pharm.* 5:767(1973), sodium diphenylhydantoin is reacted with methyl 5-bromovalerate followed by acid hydrolysis to yield the following:

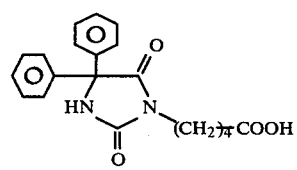

Morphine

Morphine free base is treated with sodium β-chloroacetate according to the method of Spector et al, *Science* 168:1347 (1970) to yield a suitable carboxylic acid derivative.

Nicotine

According to the method of Langone et al, *Biochem.* 12(24): 5025(1973), trans-hydroxymethylnicotine and succinic anhydride are reacted to yield the following:

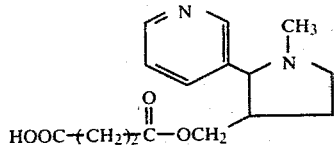

Androgens

Suitable carboxylic acid derivatives of testosterone and androstenedione linked through either the 1- or 7-position on the steroid nucleus are prepared according to the method of Bauminger et al, *J. Steroid Biochem.* 5:739(1974). Following are representative testosterone derivatives:

1-position

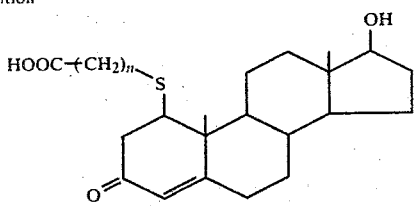

7-position

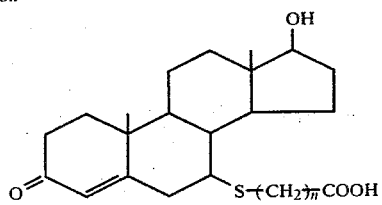

Estrogens

Suitable carboxylic acid derivatives of estrogens, e.g., estrone, estradiol and estriol, are prepared according to the method of Bauminger et al, supra, as represented by the following estrone derivative:

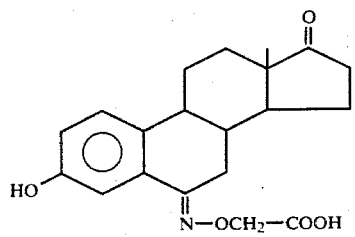

Progesterones

Suitable carboxylic acid derivatives of progesterone and its metabolites linked through any of the 3-, 6- or 7-positions on the steroid nucleus are prepared according to the method of Bauminger et al, supra, as represented by the following progesterone derivatives:

3-position

-continued

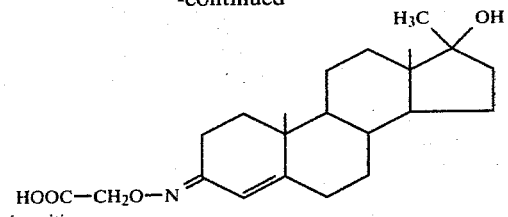

6-position

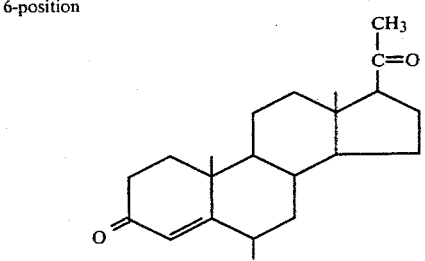

7-position

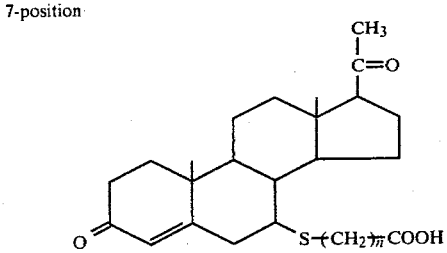

The methods described above are but examples of the many known techniques for forming suitable carboxylic acid derivatives of haptens of analytical interest. The principal derivation techniques are discussed in *Clin. Chem.* 22:726(1976) and include esterification of a primary alcohol with succinic anhydride [Abraham and Grover, *Principles of Competitive Protein-Binding Assays*, ed. Odell and Daughaday, J. B. Lippincott Co. (Philadelphia 1971) pp. 140–157], formation of an oxime from reaction of a ketone group with carboxylmethyl hydroxylamine [*J. Biol. Chem.* 234:1090(1959)], introduction of a carboxyl group into a phenolic residue using chloroacetate [*Science* 168:1347(1970)], and coupling to diazotized p-aminobenzoic acid in the manner described in *J. Biol. Chem.* 235:1051 (1960).

The hereinbefore-described general synthetic sequence for preparing the present chemiluminescent-labeled conjugates is specifically exemplified by the following description of the preparation of the labeled thyroxine conjugate 7-[N-ethyl-N-(4-thyroxinylamido)-butyl]aminonapththalene-1,2 -dicarboxylic acid hydrazide. The reaction sequence for this synthesis is outlined in Table 1 which follows.

A. Preparation of the Labeled Conjugate

Dimethyl 7-[4-N-(Phthalimido)butyl]aminonaphthalene -1,2-dicarboxylate (3)

A solution of 14.1 grams (g) (0.05 mol) of N-(4-bromobutyl)phthalimide (1) (Aldrich Chemical Co., Milwaukee, Wisconsin USA) and 25.0 g (0.1 mol) of dimethyl 7-aminonaphthalene-1,2-dicarboxylate (2) [Gundermann et al, *Justus Liebig's Annalen der Chemie* 684:127(1965)] in 100 milliliters (ml) of 2,2,2,-trifluoroethanol was refluxed under argon for 16 hours. Evaporation gave a residue that was partitioned between 400 ml of ether and 300 ml of water (H₂O). The ether phase was separated, dried, and evaporated. The resulting dark red residue was chromatographed on a column of 1200 g of silica gel (E. Merck, Darmstadt, West Germany) eluting with a 19:1 volume (v:v) mixture of benzene and methanol. After the first 700 ml of eluent was discarded, 20 ml fractions were collected. Fractions numbered 219 to 251 were combined and evaporated to give 9 g of the substituted carboxylate (3) as a clear red oil.

Analysis: NMR Spectrum (CDCl$_3$): δ1.7 (m, 4H), 3.9 (s, 3H), 4.0 (s, 3H). Infrared Spectrum (CDCl$_3$): 1720 cm$^-$ (carbonyl). Mass Spectrum (70 eV) m/e: 461 [MH+], 460 [M+], 429 [M+minus OCH$_3$].

TABLE 1

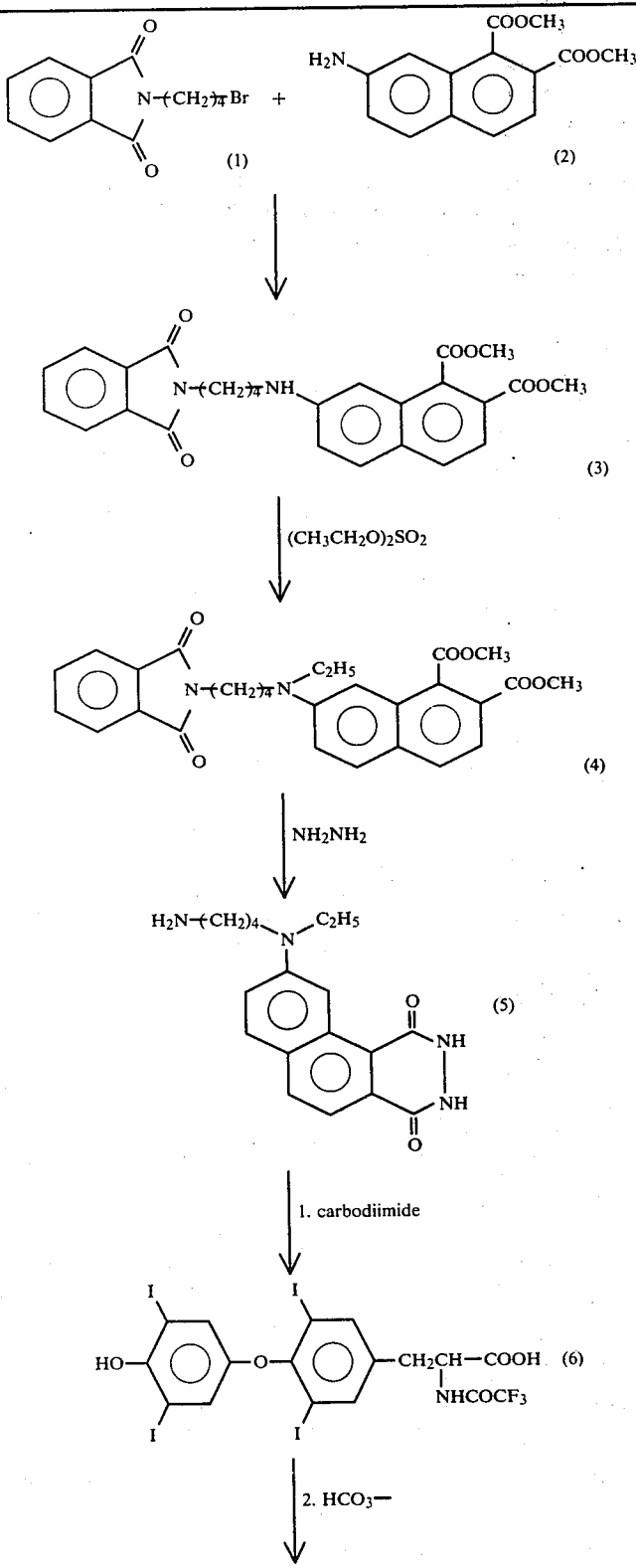

TABLE 1-continued

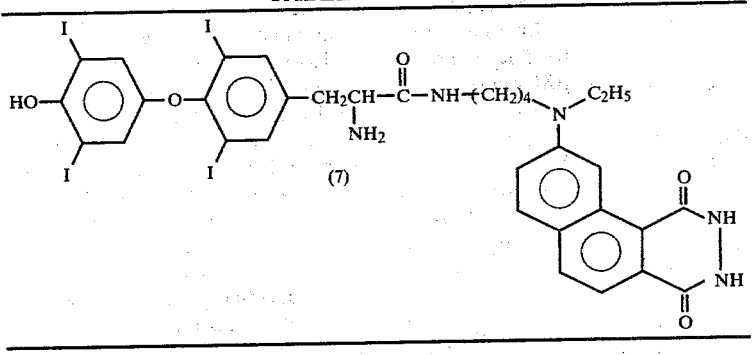

Dimethyl 7-{N-Ethyl-N-[4-(N-phthalimido)butyl]amino}naphthalene-1,2-dicarboxylate (4)

A mixture of 9 g (0.02 mol) of the substituted carboxylate (3) and 20 ml of diethyl sulfate was heated at 130° C. for two hours under argon. The dark solution was poured into a beaker of crushed ice containing 200 ml of saturated aqueous sodium bicarbonate solution. When all the ice had melted, the mixture was extracted with three 250 ml volumes of ether. The ether extracts were combined, dried, and evaporated to give a red oil. The oil was chromatographed on a column of 600 g of silica gel eluting with a 19:1 (v:v) mixture of benzene and methanol and the light yellow fractions combined and evaporated. Excess diethyl sulfate was removed by evaporative sublimation at 50° C. and reduced pressure at 0.01 millimeters (mm) mercury leaving a residue of 4 g of the N-ethyl substituted carboxylate (4) as a light red oil.

Analysis: NMR Spectrum (CDCl$_3$): δ3.9 (s,3H), 4.1 (s, 3H). Mass Spectrum (70 eV) m/e: 489 [MH+], 488 [M+], 457 [M+minus OCH$_3$].

7-[N-(4-Aminobutyl)-N-ethyl]aminonaphthalene-1,2-dicarboxylic Acid Hydrazide (5)

A mixture of 4 g (0.008 mol) of the N-ethyl substituted carboxylate (4), 15 ml of 85% hydrazine, and 50 ml of methanol was refluxed for three hours. When cool, the mixture was evaporated to dryness on a rotary evaporator and the crystalline residue scraped out and dried overnight at 80° C. under high vacuum. The resulting dark solid was chromatographed on a column of 200 g of silica gel (E. Merck, Darmstadt, West Germany), eluting with a 7:3 (v:v) mixture of ethanol and 1 molar (M) triethylammonium bicarbonate and collecting 20 ml fractions. Fractions numbered 25 to 75 were combined and evaporated to give a yellow solid. After two recrystallizations from pyridine, there was collected 1.1 g of the amino-hydrazide (5) as five yellow crystals, melting point (m.p.) 246°-247° C.

Analysis: Calculated for C$_{18}$H$_{22}$N$_4$O$_2$: C, 66.24; H, 6.80; N, 17.17. Found: C, 66.05; H, 6.69; N, 17.65.

NMR Spectrum (d$_6$-DMSO): δ1.1 (m, 3H), 1.5 (m, 4H).

Infrared Spectrum (KCl): 1615 cm$^{-1}$ (carbonyl).

The efficiency of the amino-derivative (5) of the label in a chemiluminescent reaction and the detection limit of such derivative were determined as follows.

In determining efficiency, the label derivative and luminol (5-amino-2,3-dihydrophthalazine-1,4-dione) were oxidized individually at several levels in the picomolar range and related to the peak light intensities by a graph plot. Linear portions of the resulting curves allowed calculation of change in peak light intensity per unit concentration for the label derivative and for luminol. Efficiency of the label derivative was expressed as a percentage of the slope produced with luminol.

Reaction mixtures (150 μl) of the following composition were assembled in 6×50 mm test tubes mounted in a Dupont 760 Luminescence Biometer (E. I. duPont de Nemours and Co., Wilmington, Delaware USA) with a sensitivity setting of 820:50 mM sodium hydroxide, 57.5 mM barbital adjusted to pH 8.6, 0.27 μM microperoxidase (Sigma Chemical Co., St. Louis, Missouri USA) and either the amino-derivative of the label or luminol at varying concentrations in the picomolar (pM) range (diluted with H$_2$O from a stock solution at 1 mM in 0.1 M sodium carbonate, pH 10.5). The final pH of the reaction mixtures was 12.6. Each mixture was incubated 10 minutes at room temperature and 10 μl of 90 mM hydrogen peroxide in 10 mM Tris-HCl buffer [tris-(hydroxymethyl)-aminomethane hydrochloride], pH 7.4 was added to initiate the chemiluminescent reaction. Peak light intensity values were recorded from the instrument readings. All reactions were performed in triplicate and averaged. The efficiency of the label derivative (5) was found to be 420%.

Detection limit was defined as the concentration of the label derivative that produced a peak light intensity one and a half times the background chemiluminescence in the reaction mixture. The detection limit for the label derivative (5) was found to be 0.1 pM.

N-Trifluoroacetylthyroxine (6)

A solution of 20 g [25.6 millimoles (mmol)] of L-thyroxine (Sigma Chemical Co., St. Louis, Missouri USA) in 240 ml of dry ethyl acetate containing 46 ml of trifluoroacetic acid and 7.6 ml of trifluoroacetic anhydride was stirred at 0° C. for one hour. Upon warming to room temperature and adding 200 ml of H$_2$O, a suspension formed which was then saturated with sodium chloride. The organic phase of the mixture was separated, washed with saturated aqueous sodium chloride solution, dried over anhydrous magnesium sulfate, filtered and evaporated to give 21.3 g of the N-protected thyroxine derivative (6). A sample was recrystallized from ether-pentane to give fine crystals, m.p. 233°-235° C. (decomposed).

Analysis: Calculated for C$_{17}$H$_{10}$F$_3$I$_4$NO$_5$: C, 23.39; H, 1.15; N, 1.60. Found: C, 23.23; H, 1.12; N, 1.56.

Infrared Spectrum (KCl): 1700 cm$^{-1}$ (carbonyl).

Optical Rotation [α]$_D^{25}$ = −14.97° (c 1.0, dimethylsulfoxide).

7-[N-Ethyl-N-(4-thyroxinylamido)butyl]aminonaphthalene-1,2-dicarboxylic Acid Hydrazide (7)

A solution of 1.746 g (2 mmol) of N-trifluoroacetylthyroxine (6) in 20 ml of dry pyridine was cooled to −10° C. with stirring under argon. To this solution was added 450 milligrams (mg) (2.2 mmol) of dicyclohexyl carbodiimide, followed 45 minutes later by 980 mg (3 mmol) of the amino-hydrazide (5). After stirring for 3 hours at −10° C., the reaction was allowed to warm to room temperature overnight. The reaction mixture was diluted with 10 ml of pyridine, 10 g of silica gel was added, and the solvent removed under vacuum. The resulting impregnated silica gel was placed atop a 200 g column of silica gel made up in a 7:3 (v:v) mixture of ethanol and 1 M triethylammonium bicarbonate, eluting with the same solvent mixture. After the first 400 ml of eluent was discarded, 20 ml fractions were collected. Fractions numbered 19 to 30 were combined and evaporated to give a yellow crystalline residue. This product was refluxed for 3 hours in 300 ml of 1 M triethylammonium bicarbonate to complete removal of the trifluoroacetyl protecting group. The solution was then filtered while hot. When cool, 15 g of silica gel was added and the solvent evaporated. The impregnated silica gel was placed atop a 200 g column of silica gel and eluted with a 7:3 (v:v) mixture of ethanol and 1 M triethylammonium bicarbonate, collecting 20 ml fractions. Fractions numbered 30 to 50 were combined and evaporated to give 910 mg of the labeled thyroxine conjugate (7) as a yellow solid. A 110 mg sample was chromatographed on a 45×3.2 centimeter (cm) column of Sephadex LH-20 (Pharmacia Fine Chemicals, Uppsala, Sweden), eluting with methanol. Fractions of 7 ml volume were collected and those numbered 64 to 76 were combined and evaporated to give 60 mg of the labeled conjugate (7) as a yellow solid, m.p. 218° C. (decomposed).

Analysis: Calculated for $C_{33}H_{31}I_4N_5O_5$: C, 36.52; H, 2.88; I, 46.77; N, 6.45. Found: C, 35.61; H, 3.02; I, 44.69; N, 6.25.

B. Binding Assay for Thyroxine

Competitive binding reaction mixtures (200 μl) were assembled in triplicate by combining the following reagents: 50 μl of 10 nM labeled conjugate (7) in 75 mM barbital buffer (pH 8.6), 50 μl of a preparation of antibody to thyroxine in the same buffer, varying volumes of 54.8 nM thyroxine in the same buffer, and a sufficient volume of the buffer to make a final volume of 200 μl. After a 10 minute incubation at room temperature, the free- and bound-species of the labeled conjugate were separated for each reaction mixture by applying a 150 μl aliquot to small Sephadex G-25 (Pharmacia Fine Chemicals, Uppsala, Sweden) columns. The columns had a bed volume of 1.5 ml and were pre-washed with successive 3 ml volumes of 7% acetic acid (3 times), $H_2O$ 0.1 M sodium hydroxide (3 times), and 75 mM of the barbital buffer. The bound-species of the labeled conjugate was eluted from the column with 1.5 ml of the barbital buffer leaving the free-species in the column.

An aliquot (95 μl) of each column effluent was added to 55 μl of a solution of 134 mM sodium hydroxide, 0.73 μM microperoxidase, and 27 mM barbital in a 6×50 mm test tube. After a 10 minute incubation at room temperature, each tube was placed in the Dupont 760 Biometer and 10 μl of 90 mM hydrogen peroxide in 10 mM Tris-HCl buffer (pH 7.4) was added. The resulting peak intensity of the light produced in the chemiluminescent reaction was recorded from the instrument reading. Each binding mixture was monitored in triplicate to give a total of 9 individual peak light intensity values which were averaged for each different volume of thyroxine added to the initial reaction mixture.

The peak intensity values were also related as a percentage of total labeled conjugate in the bound-species by ratioing such values to the peak light intensity measured in the chemiluminescent reaction using 95 μl of 0.25 nM labeled conjugate in place of the column effluent. Background chemiluminescence in the monitoring reaction was found to be 0.3 peak intensity units.

The relationships of the amount of thyroxine in the binding reaction to peak light intensity and percent of labeled conjugate in the bound-species are shown in Table 2 below.

TABLE 2

| volume of thyroxine solution added (μl) | peak light intensity | percent in bound-species |
|---|---|---|
| 0 | 26.5 | 63.1 |
| 5 | 25.3 | 59.5 |
| 10 | 23.3 | 55.5 |
| 20 | 23.7 | 56.4 |
| 40 | 19.1 | 45.4 |
| 60 | 14.7 | 35.0 |
| 80 | 13.7 | 32.6 |

The results demonstrate that the labeled conjugate of the present invention is useful in binding assays for determining a ligand in a liquid medium.

What is claimed is:

1. A compound of the formula:

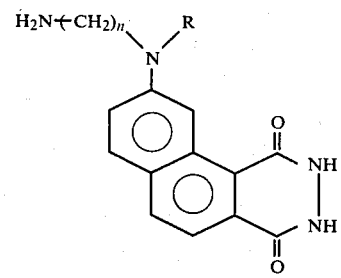

wherein R is hydrogen or straight chain alkyl containing 1–4 carbon atoms and n=2–6.

2. The compound of claim 1 wherein n=4.

3. The compound of claim 2 wherein R is ethyl.